US00PP11053P

United States Patent [19]

Brown

[11] Patent Number: Plant 11,053

[45] Date of Patent: Sep. 7, 1999

[54] AGLAONEMA PLANT NAMED 'WHITE LANCE'

[75] Inventor: B. Frank Brown, Valkaria, Fla.

[73] Assignee: Sunshine Foliage World, Zolfo Springs, Fla.

[21] Appl. No.: 09/004,129

[22] Filed: Jan. 7, 1998

[51] Int. Cl.[6] ..... A01H 5/00

[52] U.S. Cl. ..... Plt./376

[58] Field of Search ..... Plt./376

*Primary Examiner*—Howard J. Locker
*Assistant Examiner*—Melissa L. Kimball
*Attorney, Agent, or Firm*—C. A. Whealy

[57] ABSTRACT

A new and distinct cultivar of Aglaonema named 'White Lance' particularly characterized by its mostly upright and somewhat outwardly arching plant habit; dense and full appearance; propensity to readily produce divisions; upper leaf surfaces that are glossy silver green with dark green margins; relatively long and lanceolate leaves; light green petioles with darker green spots/splotches on the wings; low temperature tolerance; and resistance to diseases common to Aglaonema.

1 Drawing Sheet

The present invention relates to a new and distinct cultivar of Aglaonema plant, botanically known as Aglaonema hybrid, and hereinafter referred to by the cultivar name White Lance.

The new Aglaonema is a product of a planned breeding program conducted by the inventor in Valkaria, Fla. The objective of the breeding program was to develop new lanceolate leaf-shaped Aglaonemas with a full and dense appearance. The new Aglaonema originated from a cross made by the inventor in 1988 of the Aglaonema hybrid cultivar Bayonet (not patented) as the female, or seed, parent with the Aglaonema hybrid cultivar Ernesto's Favorite (not patented) as the male, or pollen, parent. The cultivar White Lance was discovered and selected by the inventor as a seedling within the progeny of the stated cross in a controlled environment in Valkaria, Fla.

Compared to plants of the female parent cultivar, Bayonet, leaves of plants of the new Aglaonema are shorter and narrower. In addition, leaves of plants of the cultivar Bayonet do not have the distinct dark green leaf margin characteristic of plants of the new Aglaonema.

Compared to plants of the male parent cultivar, Ernesto's Favorite, leaves of plants of the new Aglaonema are much narrower and have a narrower dark green leaf margin.

Asexual propagation of the new cultivar by divisions at Zolfo Springs, Fla. since 1988, has shown that the unique features of this new Aglaonema plant are stable and reproduced true to type in successive generations.

The new Aglaonema has not been observed under all possible environmental conditions. The phenotype may vary somewhat with variations in environment such as temperature, light intensity, fertilizer rate, and/or irrigation amount and frequency without, however, any variance in genotype.

The following traits have been repeatedly observed and are determined to be the unique characteristics of 'White Lance'. These characteristics in combination distinguish 'White Lance' as a new and distinct cultivar:

1. Plants of the new Aglaonema are mostly upright and somewhat outwardly arching in plant habit.
2. Petioles are closely spaced giving plants a dense and full appearance.
3. Plants of the new Aglaonema readily produce divisions.
4. The upper surfaces of mature leaves of plants of the new Aglaonema are glossy silver green with dark green margins.
5. The leaves of the new Aglaonema are relatively long and lanceolate.

6. Mature leaves of plants of the new Aglaonema have light green petioles with darker green spots/splotches on the wings.
7. Plants of the new Aglaonema are tolerant of low temperatures, that is, ambient temperatures of about 4° C. do not cause foliar damage.
8. Plants of the new Aglaonema are resistant to diseases common to Aglaonema.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical plant of 'White Lance' in a 25.5-cm container.

The photograph at the bottom of the sheet comprises a close-up view of the upper surface of a mature leaf. Leaf colors in the photographs may appear different from the actual colors due to light reflectance.

DETAILED BOTANICAL DESCRIPTION

The following observations, measurements and comparisons describe plants grown in Zolfo Springs, Fla., under a polypropylene-covered shadehouse and conditions which closely approximate those used in horticultural practice. Plants were grown under day temperatures ranging from 21 to 38° C. and night temperatures ranging from 7 to 21° C. The polypropylene shade provided a 84 percent decrease in ambient light level. In the following description, color references are made to The Royal Horticultural Society Colour Chart except where general terms of ordinary dictionary significance are used.

Botanical classification: Aglaonema hybrid cultivar White Lance.

Parentage:

*Female, or seed, parent.*—Aglaonema hybrid cultivar Bayonet, not patented.

*Male, or pollen, parent.*—Aglaonema hybrid cultivar Ernesto's Favorite, not patented.

Propagation:

*Type.*—By division and by cuttings.

*Time to initiate roots*.—About 19 and 27 days at 30 and 21° C., respectively.

*Time to develop roots*.—About 27 and 41 days at 30 and 21° C., respectively.

*Rooting habit*.—Numerous fleshy white roots.

Plant description:

*Plant shape*.—Mostly upright and somewhat outwardly arching. Closely-spaced leaves give plants a full and dense appearance.

*Growth habit*.—Erect when young, becoming somewhat outwardly arching. Appropriate for 25.5-cm containers. Plants readily produce divisions.

*Plant size*.—Height, soil surface to top of leaf canopy: About 65 cm. Width: About 60 cm.

*Plant vigor*.—Moderate.

*Stem description*.—Diameter at soil surface: About 1.75 cm. Internode length: About 1.5 cm. Color, mature: Green, 144A, with yellow green spots.

*Foliage description*.—Shape: Lanceolate. Length, fully expanded: About 30 cm. Width, fully expanded: About 5 cm. Margin: Entire. Apex: Acuminate. Base: Cuneate. Aspect: Mostly flat, slightly undulating. Texture: Leathery, smooth, glabrous, glossy on both surfaces. Color: Young, upper surface: Center: Green, close to 137C and 147C. Dark green spots/streaks and margin: Greener than 137A. Young, lower surface: Green, close to 137C. Mature, upper surface: Center: Silver green, close to 191A. Dark green spots/streaks and margin: 147A to darker than 147A. Mature, lower surface: Background: Green, close to 146A. White spots/streaks: 155A. Petiole length, primary shoot: About 20.5 cm. Petiole diameter at apex: About 5 mm. Petiole diameter at base: About 1 cm. Petiole wing: Apparent on lower 67% of mature leaf petiole, about 14 cm in length and about 5 mm in width. Petiole color: Young: Light green, 144D. Mature: Light green, 144D, with darker green, 144A, spots/streaks mostly on wings. Venation, midvein: Mature, upper surface: Same as leaf color or light green, close to 144D. Mature, lower surface: 144D/145C.

*Inflorescence*.—Typical of Aglaonema, no commercial significance.

Disease tolerance: Plants of the new Aglaonema are resistant to diseases common to Aglaonema.

Low temperature tolerance: Plants of the new Aglaonema are tolerant of low temperatures, that is, ambient temperatures of about 4° C. do not cause foliar damage.

It is claimed:

1. A new and distinct cultivar of Aglaonema plant named 'White Lance', as illustrated and described.

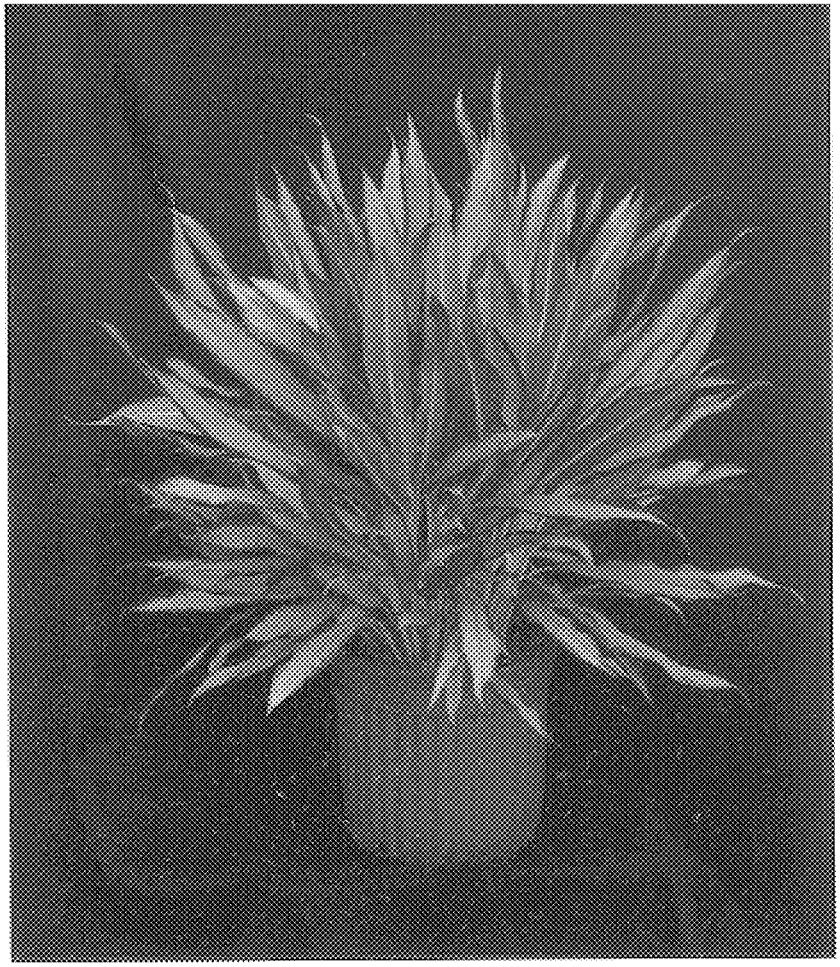
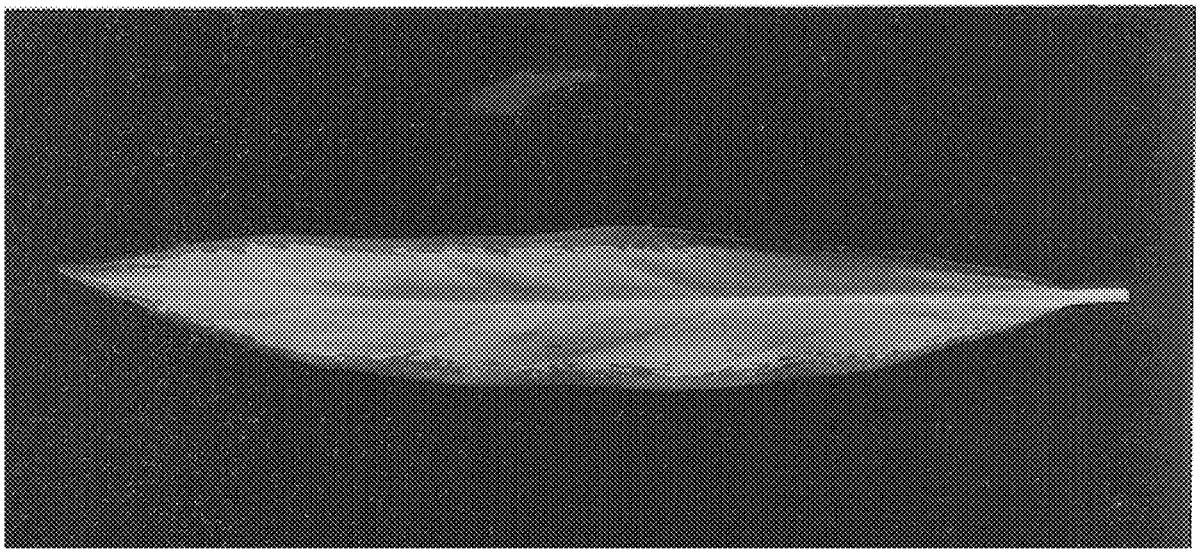

* * * * *